US006660275B2

(12) United States Patent
Murdin et al.

(10) Patent No.: US 6,660,275 B2
(45) Date of Patent: Dec. 9, 2003

(54) CHLAMYDIA ANTIGENS AND CORRESPONDING DNA FRAGMENTS AND USES THEREOF

(75) Inventors: Andrew D. Murdin, Ontario (CA); Raymond P. Oomen, Ontario (CA); Pamela L. Dunn, Ontario (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/361,443

(22) Filed: Jul. 26, 1999

(65) Prior Publication Data

US 2002/0150591 A1 Oct. 17, 2002

Related U.S. Application Data

(60) Provisional application No. 60/094,195, filed on Jul. 27, 1998.

(51) Int. Cl.[7] .................. A61K 39/00; A61K 39/38; A61K 39/02; A61K 39/118; G01N 38/571
(52) U.S. Cl. .................. 424/263.1; 424/184.1; 424/185.1; 424/190.1; 424/263.1; 435/7.36; 435/89; 435/91.1; 435/91.31; 435/91.42; 435/91.4
(58) Field of Search .................. 424/263.1, 184.1, 424/185.1, 190.1; 435/7.36, 89, 91.1, 91.31, 91.42, 91.4; 514/44; 935/77, 79, 80

(56) References Cited

FOREIGN PATENT DOCUMENTS

WO    WO 99/27105    6/1999

OTHER PUBLICATIONS

Attwood. 2000. Science. 290:471–473.*
Gerhold et al. 1996. BioEssays. 18(12):973–981.*
Wells et al. 1997. J. of Leukocyte Bio. 61: 545–550.*
Longbottom, et al. EMBL Database Entry XP002135734 (Nov. 5, 1996).
Longbottom, et al. Infec. Immun. XP00885982, 1317–1324, vol. 66, No. 4 (1998).
Birkeland, et al. EMBL Database Entry XP002135735 (Apr. 26, 1999).
Kalman et al. EMBL Database Entry XP002135736 (May 1, 1999).
Kalman et al. Nature Genetics. XP000853883, 385–389, vol. 21, No. 4 (1999).
Griffais, EMBL Database Entry XP002135737 (Sep. 15, 1999).
Christianson, et al. Scandinavian J. XP002088986, 5–10, Suppl. 104 (Jan. 1, 1997).
Kanamoto, et al. Microbiology XP002088968, 495–498, vol. 37, No. 6 (Jan. 1, 1993).
Campbell, et al. Clinical Microbiology XP002057608, 1261–1264, vol. 28, No. 6, (Jun. 1, 1990).
Campbell, et al. Infec. Immunity XP000083693, 93–97, vol. 58, No. 1, (Jan. 1, 1999).
Kalman, et al., Nature Genetics, 21, 385–389 (1999).
Magee, et al., Infection and Immunity, 63:2, 516–521 (1995).
Landers, et al., Infection and Immunity, 59:10, 3774–3777 (1991).
Jackson, et al., Abstracts of the 36th ICAAC, 272 (1996).
Magee, et al., Regional Immunology, 5, 305–311 (1993).
Igletseme, et al., Regional Immunology, 5, 317–324 (1993).
Jones, et al., Vaccine, 13:8, 715–723 (1995).
Pal, et al., Infection and Immunity, 64:12, 5341–5348 (1996).
Hahn, et al., The Journal of the American Medical Association, 266:2, 225–230 (1991).
Allegra, et al., European Respiratory Journal, 7:2, 2165–2168 (1994).
Björnsson, et al., Scandinavian Journal of Infectious Diseases, 28:1, 63–69 (1996).
Hahn, The Journal of Family Practice, 41:4, 345–351 (1995).
Hahn, et al., Epidemiology Infection, 117:3, 513–517 (1996).
Hahn, et al., Annals of Allergy, Asthma, and Immunology, 80:1, 45–49 (1998).
Fong, et al., Journal of Clinical Microbiology, 35:1, 48–52 (1997).
Ramirez, et al., Annals of Internal Medicine, 125:12, 979–982 (1996).
Chiu, et al., Circulation, 96:7, 2144–2148 (1997).
Campbell, et al., The Journal of Infectious Diseases, 172:2, 585–588 (1995).
Kuo, et al., Arteriosclerosis and Thrombosis, 13:10, 1501–1504 (1993).
Kuo, et al., The Journal of Infectious Diseases, 167:4, 841–849 (1993).
Melnick, et al., The American Journal of Medicine, 95, 499–504 (1993).
Saikku, et al., Annals of Internal Medicine, 116:4, 273–278 (1992).
Grayston, et al., The Journal of Infectious Diseases, 168:5, 1231–1235 (1993).
Campos, et al., Investigative Opthhalmology & Visual Science, 36:8, 1477–1491 (1995).

(List continued on next page.)

Primary Examiner—Lynette R. F. Smith
Assistant Examiner—JaNa Hines
(74) Attorney, Agent, or Firm—Mintz, Levin, Cohn, ferris, Glovsky & Popeo, P.C.; Ivor R. Elrifi; Nicholas P. Triano, III

(57) ABSTRACT

The present invention provides a method of nucleic acid, including DNA, immunization of a host, including humans, against disease caused by infection by a strain of Chlamydia, specifically *C. pneumoniae*, employing a vector, containing a nucleotide sequence encoding a CPN100605 polypeptide of a strain of *Chlamydia pneumoniae* and a promoter to effect expression of the CPN100605 polypeptide in the host. Modifications are possible within the scope of this invention.

5 Claims, 8 Drawing Sheets

OTHER PUBLICATIONS

Grayston, et al., The Journal of Infectious Diseases, 161:4, 618–625 (1990).
Marrie, Clinical Infectious Diseases, 18:4, 501–515 (1994).
Wang et al., Chlamydial Infections, 329–333 (1986).
Saikku, et al. The Lancet, 2:8618, 983–985 (1988).
Thom, et al., The Journal of the American Medical Association, 268:1, 68–72 (1992).
Linnanmäki, et al., Circulation, 87:4, 1130–1134 (1993).
Bachmaier, et al., Science, 283, 1335–1339 (1999).
Iijima, et al., Journal of Clinical Microbiology, 32:3, 583–588 (1994).
Campbell, et al., Journal of Clinical Microbiology, 28:6, 1261–1264 (1990).
Melgosa, et al., FEMS Microbiology Letters, 112:2, 199–204 (1993).
Watson, et al., Microbiology, 141, 2489–2497 (1995).
Watson, et al., Nucleic Acids Research, 18:7, 5299 (1990).
Melgosa, et al., Infection and Immunity, 62:3, 880–886 (1994).
Takase, et al., Journal of Bacteriology, 169:12, 5692–5699 (1987).
Cagnon et al., Protein Engineering, 4:7, 843–847 (1991).
Casey, et al., Nucleic Acids Research, 4:5, 1539–1553 (1977).
Kunkel, Proc. Natl. Acad. Sci. USA, 82, 488–492 (1985).
Langeveld, et al., Vaccine, 12:15, 1994.
Snijders, et al., The Journal of General Virology, 72:3, 557–565 (1991).
Dion, et al., Virology, 179:1, 474–477 (1990).
Hughes, et al., Infection and Immunity, 60:9, 3497–3503 (1992).
Wiedmann–Al–Ahmad, et al., Clinical and Diagnostic Laboratory Immunology, 4:6, 700–704 (1997).
McCafferty, et al., Infection and Immunity, 63:6, 2387–2389 (1995).
Campbell, et al., Infection and Immunity, 58:1, 93–97 (1990).
Cotter, et al., Infection and Immunity, 63:12, 4704–4714 (1995).
Chlamydia Genome Project, http://chlamydia–www.berkeley.edu:4231, updated Sep. 23, 1999.
Shor, et al, S AFR Med Journal, 82, 158–161 (1992).

\* cited by examiner

```
atg aaa att aca gtc aat cgg ggt tta gat tta tcc tta caa ggg tct    48
Met Lys Ile Thr Val Asn Arg Gly Leu Asp Leu Ser Leu Gln Gly Ser
    Ile Thr Val Asn Arg Gly Leu Asp Leu Ser Leu Gln Gly Ser
 1           5                  10                  15 ccc aaa gaa tct ggt ttc tat aac aaa atc gat cca gaa ttc gta tct    96
Pro Lys Glu Ser Gly Phe Tyr Asn Lys Ile Asp Pro Glu Phe Val Ser
Pro Lys Glu Ser Gly Phe Tyr Asn Lys Ile Asp Pro Glu Phe Val Ser
            20                  25                  30 ata gac tta agg cca ttc caa cct tta tct ctt aaa ctt aag gta gag   144
Ile Asp Leu Arg Pro Phe Gln Pro Leu Ser Leu Lys Leu Lys Val Glu
Ile Asp Leu Arg Pro Phe Gln Pro Leu Ser Leu Lys Leu Lys Val Glu
        35                  40                  45 caa gga gat gcg gtc tgt tca gga gct cct ata gca gaa tac aag cac   192
Gln Gly Asp Ala Val Cys Ser Gly Ala Pro Ile Ala Glu Tyr Lys His
Gln Gly Asp Ala Val Cys Ser Gly Ala Pro Ile Ala Glu Tyr Lys His
    50                  55                  60 ttt cct aac acc tac att acc tct cac gtt tca gga gta gtt acc gct   240
Phe Pro Asn Thr Tyr Ile Thr Ser His Val Ser Gly Val Val Thr Ala
Phe Pro Asn Thr Tyr Ile Thr Ser His Val Ser Gly Val Val Thr Ala
 65                  70                  75                  80 ata cga cgt gga aat aaa cgt tct ctt tta gat gtc atc att aag aaa   288
Ile Arg Arg Gly Asn Lys Arg Ser Leu Leu Asp Val Ile Ile Lys Lys
Ile Arg Arg Gly Asn Lys Arg Ser Leu Leu Asp Val Ile Ile Lys Lys
                85                  90                  95 act cct ggt cct aca tct aca gaa tat acg tat gat ctc caa act ctc   336
Thr Pro Gly Pro Thr Ser Thr Glu Tyr Thr Tyr Asp Leu Gln Thr Leu
Thr Pro Gly Pro Thr Ser Thr Glu Tyr Thr Tyr Asp Leu Gln Thr Leu
            100                 105                 110 tca cgt tca gat ctt tcc gaa atc ttt aag gaa aat ggg ctc ttt gca   384
Ser Arg Ser Asp Leu Ser Glu Ile Phe Lys Glu Asn Gly Leu Phe Ala
Ser Arg Ser Asp Leu Ser Glu Ile Phe Lys Glu Asn Gly Leu Phe Ala
        115                 120                 125
```

FIG. 1A

```
tta atc aaa caa cgt cct ttt gat att ccc gca att cca aca caa act    432
Leu Ile Lys Gln Arg Pro Phe Asp Ile Pro Ala Ile Pro Thr Gln Thr
Leu Ile Lys Gln Arg Pro Phe Asp Ile Pro Ala Ile Pro Thr Gln Thr
        130                 135                 140 ccg aga gat gtt ttc atc aat tta gct gac aat cgt cct ttt act cca    480
Pro Arg Asp Val Phe Ile Asn Leu Ala Asp Asn Arg Pro Phe Thr Pro
Pro Arg Asp Val Phe Ile Asn Leu Ala Asp Asn Arg Pro Phe Thr Pro
145                 150                 155                 160 agc cca gaa aaa cat ctg gct ctc ttt tcc tct aga gaa gaa gga ttt    528
Ser Pro Glu Lys His Leu Ala Leu Phe Ser Ser Arg Glu Glu Gly Phe
Ser Pro Glu Lys His Leu Ala Leu Phe Ser Ser Arg Glu Glu Gly Phe
                165                 170                 175 tat gta ttt gtg gta gga gtt cga gct ata gct aaa ctt ttt gga ctc    576
Tyr Val Phe Val Val Gly Val Arg Ala Ile Ala Lys Leu Phe Gly Leu
Tyr Val Phe Val Val Gly Val Arg Ala Ile Ala Lys Leu Phe Gly Leu
            180                 185                 190 cgt cct cat ata gtt ttc aga gat cgt tta act cta cct acg caa gaa    624
Arg Pro His Ile Val Phe Arg Asp Arg Leu Thr Leu Pro Thr Gln Glu
Arg Pro His Ile Val Phe Arg Asp Arg Leu Thr Leu Pro Thr Gln Glu
        195                 200                 205 cta aag aca att gct cac ctt cat acc gtt tcg gga cca ttc ccc tct    672
Leu Lys Thr Ile Ala His Leu His Thr Val Ser Gly Pro Phe Pro Ser
Leu Lys Thr Ile Ala His Leu His Thr Val Ser Gly Pro Phe Pro Ser
    210                 215                 220 gga tct cca tcg ata cat att cac agc gta gcc cct att acc aat gag    720
Gly Ser Pro Ser Ile His Ile His Ser Val Ala Pro Ile Thr Asn Glu
Gly Ser Pro Ser Ile His Ile His Ser Val Ala Pro Ile Thr Asn Glu
225                 230                 235                 240 aaa gaa gtg gta ttc aca ctg tca ttt caa gat gtc ctt act att ggc    768
Lys Glu Val Val Phe Thr Leu Ser Phe Gln Asp Val Leu Thr Ile Gly
Lys Glu Val Val Phe Thr Leu Ser Phe Gln Asp Val Leu Thr Ile Gly
                245                 250                 255
```

FIG. 1B

```
cat ctt ttc tta aag gga aga att ctg cac gag caa gtc aca gca ctt    816
His Leu Phe Leu Lys Gly Arg Ile Leu His Glu Gln Val Thr Ala Leu
His Leu Phe Leu Lys Gly Arg Ile Leu His Glu Gln Val Thr Ala Leu
                260                 265                 270 gct ggt act gca cta aaa agt tct cta aga cgc tat gtg att act aca    864
Ala Gly Thr Ala Leu Lys Ser Ser Leu Arg Arg Tyr Val Ile Thr Thr
Ala Gly Thr Ala Leu Lys Ser Ser Leu Arg Arg Tyr Val Ile Thr Thr
            275                 280                 285 aaa gga gct agc ttc tct agt tta atc aat ctt aat gac atc tcg gat    912
Lys Gly Ala Ser Phe Ser Ser Leu Ile Asn Leu Asn Asp Ile Ser Asp
Lys Gly Ala Ser Phe Ser Ser Leu Ile Asn Leu Asn Asp Ile Ser Asp
        290                 295                 300 aac gat aca tta att agc gga gat ccc tta aca gga agg cta tgc aaa    960
Asn Asp Thr Leu Ile Ser Gly Asp Pro Leu Thr Gly Arg Leu Cys Lys
Asn Asp Thr Leu Ile Ser Gly Asp Pro Leu Thr Gly Arg Leu Cys Lys
305                 310                 315                 320 aag gaa gag gaa ccc ttt tta gga ttt cga gac cat tca att tca gtc   1008
Lys Glu Glu Glu Pro Phe Leu Gly Phe Arg Asp His Ser Ile Ser Val
Lys Glu Glu Glu Pro Phe Leu Gly Phe Arg Asp His Ser Ile Ser Val
                325                 330                 335 tta cac aac cca aca aag cgg gag ttg ttt agc ttt tta aga att ggg   1056
Leu His Asn Pro Thr Lys Arg Glu Leu Phe Ser Phe Leu Arg Ile Gly
Leu His Asn Pro Thr Lys Arg Glu Leu Phe Ser Phe Leu Arg Ile Gly
            340                 345                 350 ttt aac aaa ccg aca ttt aca aaa acc tat ctc tca gga ttt ttc aag   1104
Phe Asn Lys Pro Thr Phe Thr Lys Thr Tyr Leu Ser Gly Phe Phe Lys
Phe Asn Lys Pro Thr Phe Thr Lys Thr Tyr Leu Ser Gly Phe Phe Lys
        355                 360                 365 aaa aag cgt acc tat acg aat cca gat act aac ctc cac gga gaa act   1152
Lys Lys Arg Thr Tyr Thr Asn Pro Asp Thr Asn Leu His Gly Glu Thr
Lys Lys Arg Thr Tyr Thr Asn Pro Asp Thr Asn Leu His Gly Glu Thr
    370                 375                 380
```

FIG. 1C

```
cgg ccg att att gat act gac atc tat gat aaa gtt atg ccg atg aga    1200
Arg Pro Ile Ile Asp Thr Asp Ile Tyr Asp Lys Val Met Pro Met Arg
Arg Pro Ile Ile Asp Thr Asp Ile Tyr Asp Lys Val Met Pro Met Arg
385                 390                 395                 400 att cct gta gtt cct ctg att aaa gct gta att act aaa aat ttt gat    1248
Ile Pro Val Val Pro Leu Ile Lys Ala Val Ile Thr Lys Asn Phe Asp
Ile Pro Val Val Pro Leu Ile Lys Ala Val Ile Thr Lys Asn Phe Asp
            405                 410                 415 tta gct aat gaa cta ggg ttt tta gag gtt tgt ggt gaa gat ttc gcc    1296
Leu Ala Asn Glu Leu Gly Phe Leu Glu Val Cys Gly Glu Asp Phe Ala
Leu Ala Asn Glu Leu Gly Phe Leu Glu Val Cys Gly Glu Asp Phe Ala
                420                 425                 430 tta ccc act ctt ata gat cca tct aaa aca gaa atg ctt acc ata gtc    1344
Leu Pro Thr Leu Ile Asp Pro Ser Lys Thr Glu Met Leu Thr Ile Val
Leu Pro Thr Leu Ile Asp Pro Ser Lys Thr Glu Met Leu Thr Ile Val
            435                 440                 445 aag gaa tcc tta ata gag tac gcc aag gaa tca ggg atc cta act ccc    1392
Lys Glu Ser Leu Ile Glu Tyr Ala Lys Glu Ser Gly Ile Leu Thr Pro
Lys Glu
            450                 455                 460 cat caa gat                                                         1401
His Gln Asp
His Gln Asp
465
```

FIG. 1D

Restriction Enzyme Analysis of CPN100605

```
              1           358           715          1072          1429
              |-----------|-------------|-------------|-------------|
enzyme
AciI          |_____!___!_____!_____!____!_____|
AclI          |_____!_____|
AclWI         |___!_____!_____!_____!__!!|
AcsI          |___!_____?_____!_____?_____?_!_____|
AfaI          |_____!_____!_____!__|
AflII         |___!_!_____|
AluI          |_____!_____!_?__*_____?*___?___!_____!!____|
Alw21I        |___!_____|
Alw26I        |__!_____!_____|
AlwI          |___!_____!_____!_____!__!!|
ApoI          |___!_____?_____!_____?_____?_!_____|
AseI          |_____!_____?_!_____|
AsnI          |_____!_____?_!_____|
AspHI         |____!_____|
AspI          |_____!_____|
AspS9I        |_____!_____!_____|
AsuHPI        |_____!_____!_____|
AsuNHI        |_____!_____|
AvaII         |_____!_____!_____|
BalI          |_____!_____|
BamHI         |_____!__|
BanII         |_____!_____!_____|
BanIII        |__!_____!_____|
Bbv12I        |__!_____|
BfaI          |_____!_____!!_____!_____|
BfmI          |___!__!___!_____!_____!_____|
BglII         |_____*_____|
Bme18I        |_____!_____!_____|
BmyI          |_____!____!_____|
Bsa29I        |__!_____!_____|
BsaAI         |_____!_____|
BsaBI         |_____!_____|
BsaI          |_!_____!_____|
BsaJI         |_____!_____!_|
BsaOI         |_____!_____|
Bsc4I         |_!_____!!_____|
BscBI         |_____!_____!_____!|
BscI          |__!_____!_____|
Bse1I         |_____?_____|
Bse8I         |_____!_____|
BseCI         |_!_____!_____|
BseDI         |_____!_____!__|
BseNI         |_____?_____|
BsgI          |_____!!_____|
Bsh1285I      |_____!_____|
```

```
StyI      |_____!_|
TaiI      |_____!?!__!!__?_____?__?_?_____|
TaqI      |___!_____!_____!_____|
TfiI      |__!_____!_____!_|
TruiI     |_____!_*_____!___!!_____!_____!____!_*_____!!_____!_____!__|
Tru9I     |_____!_*_____!___!!_____!_____!____!_*_____!!_____!_____!__|
TscI      |_____!?!__!!__?_____?__?_?_____|
Tsp45I    |_____!_____|
Tsp509I   |!___!_____!_!_____!_____!_____!__?__?_____?!*____|
TspEI     |!___!_____!_!_____!_____!_____!__?__?_____?!*____|
TspRI     |_____!_____|
Tth111I   |_____!_____|
Vha464I   |____!_!_____|
VspI      |_____!_____?_!_____|
XbaI      |_____!_____|
XhoII     |_____*_____!_____!_____!__!_|
XmaIII    |_____!_____|
```

FIG. 2D

CHLAMYDIA ANTIGENS AND CORRESPONDING DNA FRAGMENTS AND USES THEREOF

RELATED U.S. APPLICATION

The present patent application claims priority to U.S. provisional patent application Ser. No. 60/094,195, filed Jul. 27, 1998.

FIELD OF THE INVENTION

The present invention relates to Chlamydia antigens and corresponding DNA molecules, which can be used in methods to prevent and treat disease caused by Chlamydia infection in mammals, such as humans.

BACKGROUND OF THE INVENTION

Chlamydiae are prokaryotes. They exhibit morphologic and structural similarities to Gram negative bacteria including a trilaminar outer membrane, which contains lipopolysaccharide and several membrane proteins. Chlamydiae are differentiated from other bacteria by their morphology and by a unique developmental cycle. They are obligate intracellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells they were long thought to be viruses. However, they have many characteristics in common with other bacteria: (1) they contain both DNA and RNA, (2) they divide by binary fission, (3) their cell envelopes resemble those of other Gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man, and other mammals, and these strains can be distinguished on the basis of host range, virulence, pathogenesis, and antigenic composition. There is strong homology of DNA within each species, but surprisingly little between species, suggesting long-standing evolutionary separation.

*C. trachomatis* has a high degree of host specificity, being almost completely limited to man; it causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *C. psittaci,* but subsequently recognized to be a new species. *C. pneumoniae* is antigenically, genetically, and morphologically distinct from other Chlamydia species (*C. trachomatis, C. pecorum* and *C. psittaci*). It shows 10% or less DNA sequence homology with either of *C. trachomatis* or *C. psittaci* and so far appears to consist of only a single strain, TWAR.

*C. pneumoniae* is a common cause of community acquired pneumonia, less frequent only than *Streptococcus pneumoniae* and *Mycoplasma pneumoniae*. Grayston et al., *J. Infect. Dis.* 168: 1231 (1995); Campos et al., *Invest. Ophthalmol. Vis. Sci.* 36: 1477 (1995), each incorporated herein by reference. It can also cause upper respiratory tract symptoms and disease, including bronchitis and sinusitis. See, e.g., Grayston et al., *J. Infect. Dis.* 168: 1231 (1995); Campos et al., *Invest. Ophthalmol. Vis. Sci.* 36: 1477 (1995); Grayston et al., *J. Infect. Dis.* 161: 618 (1990); Marrie, *Clin. Infect. Dis.* 18: 501 (1993). The great majority of the adult population (over 60%) has antibodies to *C. pneumoniae* (Wang et al., *Chlamydial Infections,* Cambridge University Press, Cambridge, p. 329 (1986)), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from formites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/day, for at least 10 to 14 days). A recently developed drug, azithromycin, is highly effective as a single-dose therapy against chlamydial infections.

In most instances, *C. pneumoniae* infection is mild and without complications, and up to 90% of infections are subacute or unrecognized. Among children in industrialized countries, infections have been thought to be rare up to the age of 5 years, although a recent study has reported that many children in this age group show PCR evidence of infection despite being seronegative, and estimates a prevalence of 17–19% in 2–4 years old. See, Normann et al., *Acta Paediatrica,* 87: 23–27 (1998). In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 years. In the USA for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease. See, Saikku et al., *Lancet* 2: 983 (1988); Thom et al., *JAMA* 268: 68 (1992); Linnanmaki et al., *Circulation* 87: 1030 (1993); Saikku et al., *Annals Int. Med.* 116: 273 (1992); Melnick et al., *Am. J Med.* 95: 499 (1993). Moreover, the organisms has been detected in atheromas and fatty streaks of the coronary, carotid, peripheral arteries and aorta. See, Shor et al., *South African Med. J.* 82: 158 (1992); Kuo et al., *J. Infect. Dis.* 167: 841 (1993); Kuo et al., *Arteriosclerosis and Thrombosis* 13: 1500 (1993); Campbell et al., *J. Infect. Dis.* 172: 585 (1995); Chiu et al., *Circulation* 96: 2144–2148 (1997). Viable *C. pneumoniae* has been recovered from the coronary and carotid artery. Ramirez et al., *Annals Int. Med.* 125: 979 (1996); Jackson et al., Abst. K121, p272, 36th ICAAC, New Orleans (1996). Furthermore, it has been shown that *C. pneumoniae* can induce changes of atherosclerosis in a rabbit model. See, Fong et al., (1997) *Journal of Clinical Microbiolology* 35: 48. Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbation of asthma in adults, and small-scale studies have shown that prolonged antibiotic treatment was effective at greatly reducing the severity of the disease in some individuals. Hahn et al., *Ann Allergy Asthma Immunol.* 80: 45–49 (1998); Hahn et al., *Epidemiol Infect.* 117: 513–517 (1996); Bjomsson et al., *Scand J Infect Dis.* 28: 63–69 (1996); Hahn, *J. Fam. Pract.* 41: 345–351 (1995); Allegra et al., *Eur. Respir. J.* 7: 2165–2168 (1994); Hahn et al., *JAMA* 266: 225–230 (1991).

In light of these results, a protective vaccine against disease caused by *C. pneumoniae* infection would be of considerable importance. There is not yet an effective vaccine for human *C. pneumoniae* infection. Nevertheless, studies with *C. trachomatis* and *C. psittaci* indicate that this is an attainable goal. For example, mice which have recovered from a lung infection with *C. trachomatis* are protected from infertility induced by a subsequent vaginal challenge. Pal et al., *Infection and Immunity* 64: 5341 (1996). Similarly, sheep immunized with inactivated *C. psittaci* were protected from subsequent chlamydial-induced abortions and stillbirths. Jones et al., *Vaccine* 13: 715 (1995). Protection from chlamydial infections has been associated with Th1 immune responses, particularly the induction of INFγ-producing CD4+ T cells. Igietsemes et al., *Immunology* 5: 317 (1993). The adoptive transfer of CD4+ cell lines or clones to nude or SCID mice conferred protection from challenge or cleared chronic disease (Igietseme et al., *Regional Immunology* 5: 317 (1993); Magee et al., *Regional Immunology* 5: 305 (1993)), and in vivo depletion of CD4+ T cells exacerbated disease post-challenge (Landers et al., *Infection & Immunity* 59: 3774 (1991); Magee et al., *Infection & Immunity* 63: 516 (1995)). However, the presence of sufficiently high titres of neutralizing antibody at mucosal surfaces can also exert a protective effect. Cotter et al., *Infection and Immunity* 63: 4704 (1995).

The extent of antigenic variation within the species *C. pneumoniae* is not well characterized. Serovars of *C. trachomatis* are defined on the basis of antigenic variation in major outer membrane proteins (MOMP), but published *C. pneumoniae* MOMP gene sequences show no variation between several diverse isolates of the organism. See, Campbell et al., *Infection and Immunity* 58: 93 (1990); McCafferty et al., *Infection and Immunity* 63: 2387–9 (1995); Knudsen et al., Third Meeting of the European Society for Chlamydia Research, Vienna (1996). Regions of the protein known to be conserved in other chlamydial MOMPs are conserved in *C. pneumoniae*. See, Campbell et al., *Infection and Immunity* 58: 93 (1990); McCafferty et al., *Infection and Immunity* 63: 2387–9 (1995). One study has described a strain of *C. pneumoniae* with a MOMP of greater that usual molecular weight, but the gene for this has not been sequenced. Grayston et al., *J. Infect. Dis.* 168: 1231 (1995). Partial sequences of outer membrane protein 2 from nine diverse isolates were also found to be invariant. Ramirez et al., *Annals Int. Med.* 125: 979 (1996). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes. Marrie, *Clin. Infect. Dis.* 18: 501 (1993).

Many antigens recognized by immune sera to *C. pneumoniae* are conserved across all chlamydiae, but 98 kDa, 76 kDa and 54 kDa proteins may be *C. pneumoniae*-specific. Campos et al., *Invest. Ophthalmol. Vis. Sci.* 36: 1477 (1995); Marrie, *Clin. Infect. Dis.* 18: 501 (1993); Wiedmann-Al-Ahmad et al., *Clin. Diagn. Lab. Immunol.* 4: 700–704 (1997). Immunoblotting of isolates with sera from patients does show variation of blotting patterns between isolates, indicating that serotypes *C. pneumoniae* may exist. Grayston et al., *J. Infect. Dis.* 168: 1231 (1995); Ramirez et al., *Annals Int. Med.* 125: 979 (1996). However, the results are potentially confounded by the infection status of the patients, since immunoblot profiles of a patient's sera change with time post-infection. An assessment of the number and relative frequency of any serotypes, and the defining antigens, is not yet possible.

Thus, a need remains for effective compositions for preventing, treating, and diagnosing Chlamydia infections.

SUMMARY OF THE INVENTION

In one aspect, the present invention provides purified and isolated DNA molecules that encode Chlamydia which can be used in methods to prevent, treat, and diagnose Chlamydia infection. Encoded polypeptides include polypeptides having the amino acid sequence shown in SEQ ID NO:2 and 4 and the DNA molecules include SEQ ID NO:1 full-length sequence and SEQ ID NO:3—coding sequence for the mature polypeptide. Those skilled in the art will appreciate that the invention also includes DNA molecules that encode mutants, variants, and derivatives of such polypeptides, which result from the addition, deletion, or substitution of non-essential amino acids as described herein. The invention also includes RNA molecules corresponding to the DNA molecules of the invention.

In addition to the DNA and RNA molecules, the invention includes the corresponding polypeptides and monospecific antibodies that specifically bind to such polypeptides.

The present invention has wide application and includes expression cassettes, vectors, and cells transformed or transfected with the polynucleotides of the invention. Accordingly, the present invention provides (i) a method for producing a polypeptide of the invention in a recombinant host system and related expression cassettes, vectors, and transformed or transfected cells; (ii) a live vaccine vectors such as viral or bacterial live vaccine vectors, including, pox virus, alphavirus, *Salmonella typhimurium,* or *Vibrio cholerae* vector, containing a polynucleotide of the invention, such vaccine vectors being useful for, e.g., preventing and treating Chlamydia infection, in combination with a diluent or carrier, and related pharmaceutical compositions and associated therapeutic and/or prophylactic methods; (iii) a therapeutic and/or prophylactic method involving administration of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of Chlamydia in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to the drawings, in which:

FIGS. 1A–1D the nucleotide sequence (top sequences) (SEQ ID NO:1 and SEQ ID NO:3) and the deduced amino acid sequence of the CPN100605 protein from *Chiamydia pneumoniae* (full-length protein—middle sequences (SEQ ID NO:2); truncated protein-bottom sequences (SEQ ID NO:4)).

Figure 2B:
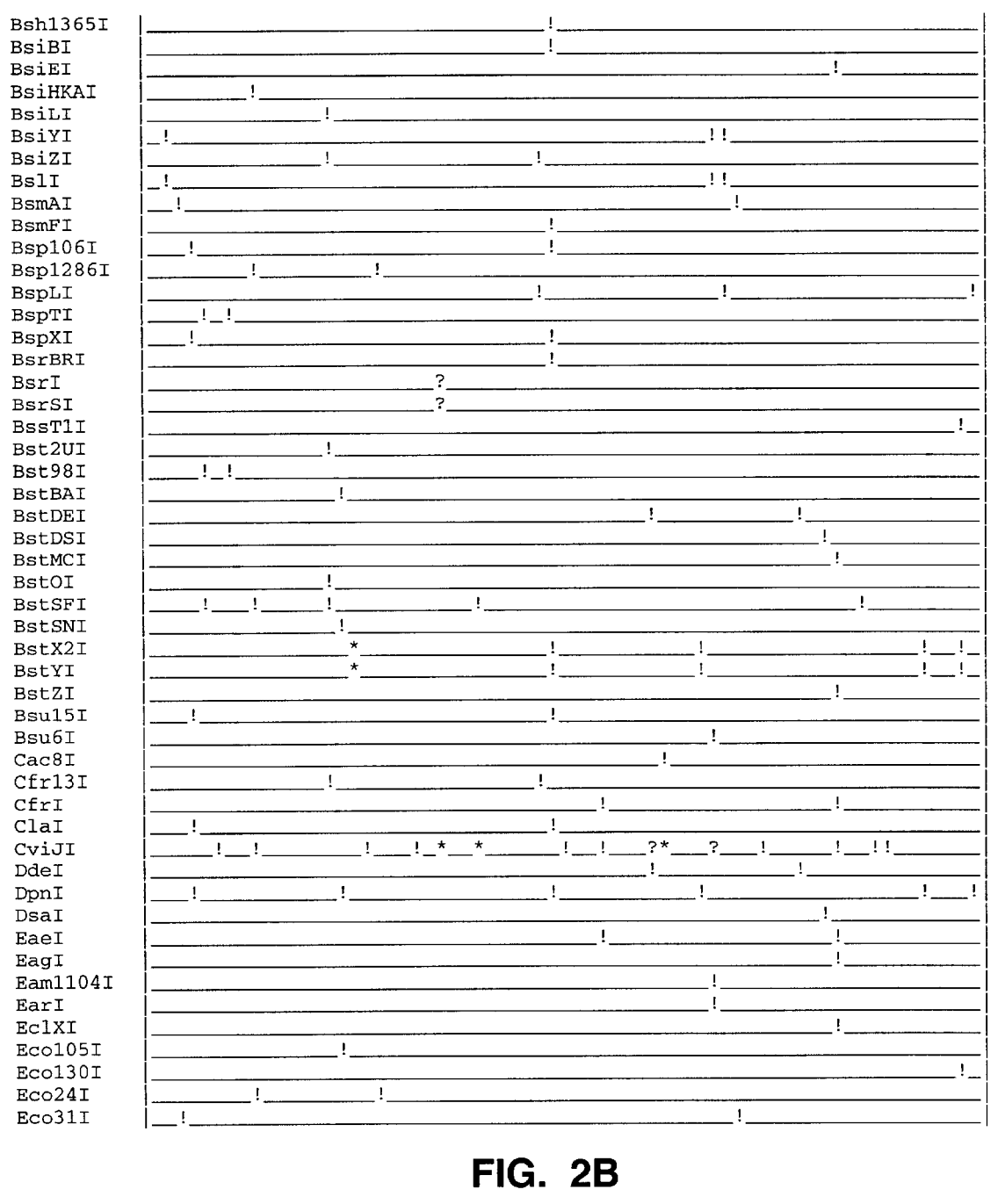
Figure 2C:
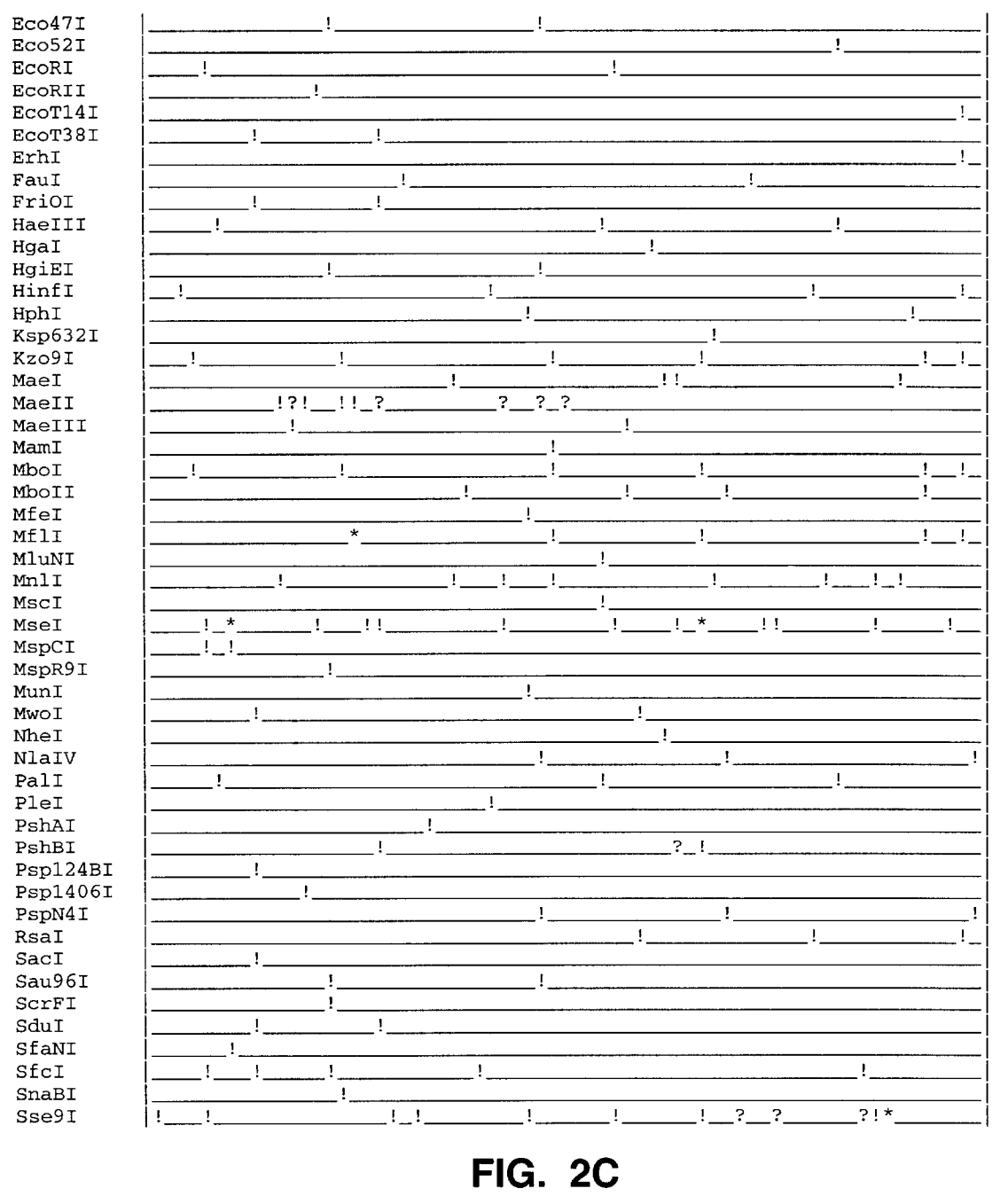

FIGS. 2A–2D show the restriction enzyme analysis of the gene encoding the *C. pneumoniae* CPN100605 gene.

DETAILED DESCRIPTION OF THE INVENTION

In the *C. pneumoniae* genome, open reading frames (ORFs) encoding chlamydial polypeptides have been identified. These polypeptides include polypeptides permanently found in the bacterial membrane structure, polypeptides that are present in the external vicinity of the bacterial membrane, include polypeptides permanently found in the inclusion membrane structure, polypeptides that are present in the external vicinity of the inclusion membrane, and polypeptides that are released into the cytoplasm of the infected cell. These polypeptides can be used in vaccination methods for preventing and treating Chlamydia infection.

According to a first aspect of the invention, there are provided isolated polynucleotides encoding the precursor and mature forms of Chlamydia polypeptides.

An isolated polynucleotide of the invention encodes a polypeptide having an amino acid sequence that is homologous to a Chlamydia amino acid sequence, the Chlamydia amino acid sequence being selected from the group consisting of the amino acid sequences as shown in SEQ ID NOS:2 or 4.

The term "isolated polynucleotide" is defined as a polynucleotide removed from the environment in which it naturally occurs. For example, a naturally-occurring DNA molecule present in the genome of the bacteria is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides could be part of a vector or a composition and still be isolated in that such a vector or composition is not part of its natural environment.

A polynucleotide of the invention can be in the form of RNA or DNA (e.g., cDNA, genomic DNA, or synthetic DNA), or modifications or combinations thereof. The DNA can be double-stranded or single-stranded, and, if single-stranded, can be the coding strand or the non-coding (anti-sense) strand. The sequence that encodes a polypeptide of the invention as shown in SEQ ID NOS:2 and 4, can be: (a) the coding sequence as shown in SEQ ID NOS:1 or 3; (b) a ribonucleotide sequence derived by transcription of (a); or (c) a different coding sequence. This latter, as a result of the redundancy or degeneracy of the genetic code, encodes the same polypeptides as the DNA molecules of which the nucleotide sequences are illustrated in SEQ ID NOS:1 and 3.

By "homologous amino acid sequence" is meant an amino acid sequence that differs from an amino acid sequence shown in SEQ ID NOS:2 or 4, only by one or more conservative amino acid substitutions, or by one or more non-conservative amino acid substitutions, deletions, or additions located at positions at which they do not destroy the specific antigenicity of the polypeptide.

Preferably, such a sequence is at least 75%, more preferably 80%, and most preferably 90% identical to an amino acid sequence shown in SEQ ID NOS:2 or 4.

Homologous amino acid sequences include sequences that are identical or substantially identical to an amino acid sequence as shown in SEQ ID NOS:2 and 4. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to introduce gaps into the sequence. Once the optimal alignment has been set up, the degree of homology (i.e., identity) is established by recording all of the positions in which the amino acids of both sequences are identical, relative to the total number of positions.

Alternatively, homology can be determined by aligning the candidate sequence and the reference sequence using an alignment tool, such as the dynamic programming algorithm described in Needleman et al., *J. Mol. Biol.* 48: 443 (1970), and the Align Program, a commercial software package produced by DNAstar, Inc., the teachings of which are incorporated by reference herein. After the initial alignment is made, it can be refined by comparison to a multiple sequence alignment of a family of related proteins. Once the alignment between the candidate and reference sequences is made and refined, a percent homology score is calculated. The individual amino acids of each sequence are compared sequentially according to their similarity to each other.

Similarity factors include similar size, shape and electrical charge. One particularly preferred method of determining amino acid similarities is the PAM250 matrix described in Dayhoff et al., 5 ATLAS OF PROTEIN SEQUENCE AND STRUCTURE 345–352 (1978 & Supp.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Preferably, a homologous sequence is one that is at least 45%, more preferably 60%, and most preferably 85% identical to (i) a coding sequence of SEQ ID NO:1, or (ii) a coding sequence of SEQ ID NO:3.

Polypeptides having a sequence homologous to one of the sequences shown in SEQ ID NOS:2 and 4, include naturally-occurring allelic variants, as well as mutants and variants or any other non-naturally-occurring variants that are analogous in terms of antigenicity, to a polypeptide having a sequence as shown in SEQ ID NOS:2 or 4.

An allelic variant is an alternate form of a polypeptide that is characterized as having a substitution, deletion, or addition of one or more amino acids that does not substantially alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS:1 and 3. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NOS:1 and 3, to the extent that the fragments retain the desired substantial antigenicity of the parent polypeptide (specific antigenicity). Polypeptide derivatives can also be constructed by large internal deletions that remove a substantial part of the parent polypeptide, while retaining the desired specific antigenicity. Generally, polypeptide derivatives should be about at least 12 amino acids in length to maintain the antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions. Hughes et al., *Infect. Immun.* 60: 3497 (1992).

Polypeptide fragments and polypeptides having large internal deletions can be used for revealing epitopes that are otherwise masked in the parent polypeptide and that may be of importance for inducing, for example, a protective T cell-dependent immune response. Deletions can also remove immunodominant regions of high variability among strains.

It is an accepted practice in the field of immunology to use fragments and variants of protein immunogens as vaccines and immunogens, as all that is required to induce an immune response to a protein may be a small (e.g., 8 to 10 amino acid) region of the protein. This has been done for a number of vaccines against pathogens other than Chlamydia. For example, short synthetic peptides corresponding to surface-exposed antigens of pathogens such as murine mammary tumor virus, peptide containing 11 amino acids (Dion et al., *Virology* 179: 474–477 (1990)); Semliki Forest virus, peptide containing 16 amino acids (Snijders et al., *J. Gen. Virol.* 72: 557–565 (1991)); and canine parvovirus, two overlapping peptides, each containing 15 amino acids (Langeveld et al., *Vaccine* 12: 1473–1480 (1994)) have been shown to be effective vaccine antigens against their respective pathogens.

Polynucleotides encoding polypeptide fragments and polypeptides having large internal deletions can be constructed using standard methods (see, e.g., Ausubel et al., CURRENT PROTOCOLS IN MOLECULAR BIOLOGY, John Wiley & Sons Inc. (1994)); for example, by PCR, including inverse PCR, by restriction enzyme treatment of the cloned DNA molecules, or by the method of Kunkel et al. (*Proc. Natl. Acad. Sci. USA* 82: 448 (1985)); biological material available at Stratagene.

A polypeptide derivative can also be produced as a fusion polypeptide that contains a polypeptide or a polypeptide derivative of the invention fused, e.g., at the N- or C-terminal end, to any other polypeptide. For construction of DNA encoding the amino acid sequence corresponding to hybrid fusion proteins, a first DNA encoding amino acid sequence corresponding to portions of the CPN100605 nucleotide sequence (SEQ ID NOS:1 or 3) is joined to a second DNA using methods described in, for example, U.S. Pat. No. 5,844,095, incorporated herein by reference. A product can then be easily obtained by translation of the genetic fusion. Vectors for expressing fusion polypeptides are commercially available, such as the pMal-c2 or pMal-p2 systems of New England Biolabs, in which the fusion peptide is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in the invention includes a polypeptide or polypeptide derivative of the invention fused to a polypeptide having adjuvant activity, such as, e.g., the subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NOS:1 and 3. Hybridization procedures are described in, e.g., Ausubel et al., CURRENT PROTOCOLS IN MOLECULAR BIOLOGY, John Wiley & Sons Inc. (1994); Silhavy et al., EXPERIMENTS WITH GENE FUSIONS, Cold Spring Harbor Laboratory Press (1984); Davis et al., A MANUAL FOR GENETIC ENGINEERING: ADVANCED BACTERIAL GENETICS, Cold Spring Harbor Laboratory Press (1980), each incorporated herein by reference. Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows:

$$Tm=81.5+0.5\times(\% \ G+C)+1.6 \ \log(\text{positive ion concentration})-0.6 \times (\% \ \text{formamide}).$$

Under appropriate stringency conditions, hybridization temperature (Th) is approximately 20–40° C., 20–25° C. or, preferably, 30–40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6× SSC containing 50% formamide or (ii) within 4–16 hours at 65° C. in an aqueous 6× SSC solution (1 M NaCl, 0.1 M sodium citrate (pH 7.0)).

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows:

$$Tm=4\times(G+C)+2(A+T).$$

For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can overexpress a polynucleotide of the invention or express it in a modified, mutated form, such as a non-toxic form, if appropriate. For vaccine compositions and uses of the proteins and peptides and encoding nucleotides of the present invention for protection against diseases caused by Chlamydia, it is not preferred to use naked DNA encoding the protein or peptides and administering these nucleotides intranasally or intramuscularly. For these proteins, it is preferred to administer the encoding nucleic acids by other routes such as intradermally and/or to formulate the encoding nucleic acids to improve (or adjuvant) the immune response. It is also preferred to include the encoding nucleic acid as part of a recombinant live vector, such as a viral or bacterial vector for use as the immunizing agent. It is also preferred to immunize with vaccine formulations comprising the proteins or peptides of the invention themselves. These vaccine formulations may include the use of adjuvants.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a prokaryotic or eukaryotic cell transformed or transfected with an expression cassette and/or vector of the invention, as well as (iv) a process for producing a polypeptide or polypeptide derivative encoded by a polynucleotide of the invention, which involves culturing a prokaryotic or eukaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from prokaryotic and eukaryotic hosts. Eukaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (SF9) cells), and plant cells. Preferably, a prokaryotic host such as *E. coli* is used. Bacterial and eukaryotic cells are available from a number of different sources to those skilled in the art, e.g., the American Type Culture Collection (ATCC; 10801 University Boulevard, Manassas, Va. 20110-2209).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., *Protein Engineering* 4: 843 (1991)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and R1pB lipidation signal peptide (Takase et al., *J. Bact.* 169: 5692 (1987)).

The expression cassette is typically part of an expression vector, which is selected for its ability to replicate in the chosen expression system. Expression vectors (e.g., plasmids or viral vectors) can be chosen from those described in Pouwels et al. (CLONING VECTORS: LABORATORY MANUAL, 85, Supp. 1987). They can be purchased from various commercial sources.

Methods for transforming/transfecting host cells with expression vectors will depend on the host system selected as described in Ausubel et al., CURRENT PROTOCOLS IN MOLECULAR BIOLOGY, John Wiley & Sons Inc. (1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumonia, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses, alphavirus, and poxviruses as well as bacterial vectors, e.g., Shigella, Salmonella, *Vibrio cholerae,* Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. Nos. 4,722,848 and 5,364,773, respectively (also see, e.g., Tartaglia et al., *Virology* 188: 217 (1992)) for a description of a vaccinia virus vector; and Taylor et al, *Vaccine* 13: 539 (1995) for a reference of a canary pox). Poxvirus vectors capable of expressing a polynucleotide of the invention can be obtained by homologous recombination as described in Kieny et al., *Nature* 312: 163 (1984) so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in three doses, four weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., *Nature* 306: 551 (1983) and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a Vibrio cholerae strain capable of expressing a polypeptide or polypeptide derivative encoded by a DNA molecule of the invention can contain, e.g., about $1\times10^5$ to about $1\times10^9$, preferably about $1\times10^6$ to about $1\times10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al., *Bio/Technology* 6: 693 (1988) and WO 92/11361. Preferred routes of administration include all mucosal routes; most preferably, these vectors are administered intranasally or orally.

Others bacterial strains useful as vaccine vectors are described in High et al., *EMBO* 11: 1991 (1992); Sizemore et al., *Science* 270: 299 (1995) (*Shigella flexneri*); Medaglini et al., *Proc. Natl. Acad. Sci. USA* 92: 6868 (1995) (*Streptococcus gordonii*); and Flynn, *Cell. Mol. Biol.* 40: 31 (1994), WO 88/6626, WO 90/0594, WO 91/13157, WO 92/1796, and WO 92/21376 (Bacille Calmettei Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae,* or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, *Molec. Cell Biol.* 5: 281(1985)). The desmin promoter (Li et al., *Gene* 78: 243 (1989), Li & Paulin, *J. Biol. Chem.* 266: 6562 (1991), and Li & Paulin, *J. Biol. Chem.* 268: 10403 (1993)) is tissue-specific and drives expression in muscle cells. More generally, useful vectors are described, i.a., WO 94/21797 and Hartikka et al., *Human Gene Therapy* 7:1205 (1996).

For DNA/RNA vaccination, the polynucleotide of the invention can encode a precursor or a mature form. When it encodes a precursor form, the precursor form can be homologous or heterologous. In the latter case, a eukaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen or a fragment, derivative, mutant, or analog thereof. A polynucleotide encoding a cytokine, such as interleukin-2 (IL-2) or interleukin-12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well-known in the art (see, e.g., LIPOSOMES: A PRACTICAL APPROACH, RPC New Ed, IRL press (1990)), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in, e.g., WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (*Nature* 356: 152 (1992)). In this case, the microparticle-coated polynucleotides can be injected via intradermal or intra-epidermal routes using a needleless injection device ("gene gun"), such as those described in U.S. Pat. Nos. 4,945,050, 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intra-epidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NOS:1 and 3.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS:1 and 3, or to a complementary or anti-sense sequence. Generally, probes are significantly shorter than full-length sequences shown in SEQ ID NOS:1 and 3; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID NOS:1 and 3 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (Nielsen et al., *Science* 254: 1497 (1991)) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., MOLECULAR CLONING: A LABORATORY MANUAL (1982) Cold Spring Harbor Laboratory Press, Cold Spring Harbor, N.Y.), Southern blot (Southern, *J. Mol. Biol.* 98: 503 (1975)), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NOS:2 and 4. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli, *Nature* 227: 680 (1970). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 $\mu$l of a preparation at about 10 $\mu$g protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 $\mu$l PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 $\mu$l of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 $\mu$g/ml is serially two-fold diluted in 50 mM Tris-HCl (pH 7.5). 100 $\mu$l of each dilution are applied to a nitrocellulose membrane 0.45 $\mu$m set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis. C. psittaci, C. pneumoniae.* or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the subcutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see LIPOSOMES: A PRACTICAL APPROACH (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 μg to about 500 mg, preferably from about 1 mg to about 200 mg. For the parenteral route of administration, the dose usually should not exceed about 1 mg, preferably about 100 μg.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., CURRENT PROTOCOLS IN IMMUNOLOGY (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., ANTIBODIES: A LABORATORY MANUAL, D. Lane, E. Harlow, Eds. (1988).

Briefly, a biological sample, such as an *C. pneumoniae* extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided: (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3 b-(N-(N',N'-dimethyl aminomethane)-carbamoyl) cholesterol (U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in Remington's Pharmaceutical Sciences, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+adjuvant can be administered on days 7, 14, 21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Equivalents

From the foregoing detailed description of the specific embodiments of the invention, it should be apparent that a unique Chlamydia antigen has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. An isolated polypeptide from a strain of Chiamydia that has at least 90% identity to SEQ ID NO:4, wherein said isolated polypeptide, when administered in an immunogenically-effective amount to a mammal, induces an immune response by said mammal against said strain of Chiamydia.

2. The polypeptide of claim 1, wherein said polypeptide has the sequence of SEQ ID NO:2.

3. A polypeptide comprising the polypeptide of claim 1 linked to a fusion polypeptide.

4. The polypeptide of claim 3, wherein the fusion polypeptide is a signal peptide.

5. The polypeptide of claim 3, wherein the fusion polypeptide comprises a heterologous polypeptide having adjuvant activity.

* * * * *

```
                          SEQUENCE LISTING

<160> NUMBER OF SEQ ID NOS:  4

<210> SEQ ID NO 1
<211> LENGTH: 1401
<212> TYPE: DNA
<213> ORGANISM: Chlamydia pneumoniae
<220> FEATURE:
<221> NAME/KEY: CDS
<222> LOCATION: (1)..(1401)
<223> OTHER INFORMATION: CPN100605

<400> SEQUENCE: 1 atg aaa att aca gtc aat cgg ggt tta gat tta tcc tta caa ggg tct       48
Met Lys Ile Thr Val Asn Arg Gly Leu Asp Leu Ser Leu Gln Gly Ser
  1               5                  10                  15 ccc aaa gaa tct ggt ttc tat aac aaa atc gat cca gaa ttc gta tct       96
Pro Lys Glu Ser Gly Phe Tyr Asn Lys Ile Asp Pro Glu Phe Val Ser
             20                  25                  30 ata gac tta agg cca ttc caa cct tta tct ctt aaa ctt aag gta gag      144
Ile Asp Leu Arg Pro Phe Gln Pro Leu Ser Leu Lys Leu Lys Val Glu
         35                  40                  45 caa gga gat gcg gtc tgt tca gga gct cct ata gca gaa tac aag cac      192
Gln Gly Asp Ala Val Cys Ser Gly Ala Pro Ile Ala Glu Tyr Lys His
     50                  55                  60 ttt cct aac acc tac att acc tct cac gtt tca gga gta gtt acc gct      240
Phe Pro Asn Thr Tyr Ile Thr Ser His Val Ser Gly Val Val Thr Ala
 65                  70                  75                  80 ata cga cgt gga aat aaa cgt tct ctt tta gat gtc atc att aag aaa      288
```

```
Ile Arg Arg Gly Asn Lys Arg Ser Leu Leu Asp Val Ile Ile Lys Lys
                85                  90                  95 act cct ggt cct aca tct aca gaa tat acg tat gat ctc caa act ctc        336
Thr Pro Gly Pro Thr Ser Thr Glu Tyr Thr Tyr Asp Leu Gln Thr Leu
            100                 105                 110 tca cgt tca gat ctt tcc gaa atc ttt aag gaa aat ggg ctc ttt gca        384
Ser Arg Ser Asp Leu Ser Glu Ile Phe Lys Glu Asn Gly Leu Phe Ala
        115                 120                 125 tta atc aaa caa cgt cct ttt gat att ccc gca att cca aca caa act        432
Leu Ile Lys Gln Arg Pro Phe Asp Ile Pro Ala Ile Pro Thr Gln Thr
    130                 135                 140 ccg aga gat gtt ttc atc aat tta gct gac aat cgt cct ttt act cca        480
Pro Arg Asp Val Phe Ile Asn Leu Ala Asp Asn Arg Pro Phe Thr Pro
145                 150                 155                 160 agc cca gaa aaa cat ctg gct ctc ttt tcc tct aga gaa gaa gga ttt        528
Ser Pro Glu Lys His Leu Ala Leu Phe Ser Ser Arg Glu Glu Gly Phe
                165                 170                 175 tat gta ttt gtg gta gga gtt cga gct ata gct aaa ctt ttt gga ctc        576
Tyr Val Phe Val Val Gly Val Arg Ala Ile Ala Lys Leu Phe Gly Leu
            180                 185                 190 cgt cct cat ata gtt ttc aga gat cgt tta act cta cct acg caa gaa        624
Arg Pro His Ile Val Phe Arg Asp Arg Leu Thr Leu Pro Thr Gln Glu
        195                 200                 205 cta aag aca att gct cac ctt cat acc gtt tcg gga cca ttc ccc tct        672
Leu Lys Thr Ile Ala His Leu His Thr Val Ser Gly Pro Phe Pro Ser
    210                 215                 220 gga tct cca tcg ata cat att cac agc gta gcc cct att acc aat gag        720
Gly Ser Pro Ser Ile His Ile His Ser Val Ala Pro Ile Thr Asn Glu
225                 230                 235                 240 aaa gaa gtg gta ttc aca ctg tca ttt caa gat gtc ctt act att ggc        768
Lys Glu Val Val Phe Thr Leu Ser Phe Gln Asp Val Leu Thr Ile Gly
                245                 250                 255 cat ctt ttc tta aag gga aga att ctg cac gag caa gtc aca gca ctt        816
His Leu Phe Leu Lys Gly Arg Ile Leu His Glu Gln Val Thr Ala Leu
            260                 265                 270 gct ggt act gca cta aaa agt tct cta aga cgc tat gtg att act aca        864
Ala Gly Thr Ala Leu Lys Ser Ser Leu Arg Arg Tyr Val Ile Thr Thr
        275                 280                 285 aaa gga gct agc ttc tct agt tta atc aat ctt aat gac atc tcg gat        912
Lys Gly Ala Ser Phe Ser Ser Leu Ile Asn Leu Asn Asp Ile Ser Asp
    290                 295                 300 aac gat aca tta att agc gga gat ccc tta aca gga agg cta tgc aaa        960
Asn Asp Thr Leu Ile Ser Gly Asp Pro Leu Thr Gly Arg Leu Cys Lys
305                 310                 315                 320 aag gaa gag gaa ccc ttt tta gga ttt cga gac cat tca att tca gtc       1008
Lys Glu Glu Glu Pro Phe Leu Gly Phe Arg Asp His Ser Ile Ser Val
                325                 330                 335 tta cac aac cca aca aag cgg gag ttg ttt agc ttt tta aga att ggg       1056
Leu His Asn Pro Thr Lys Arg Glu Leu Phe Ser Phe Leu Arg Ile Gly
            340                 345                 350 ttt aac aaa ccg aca ttt aca aaa acc tat ctc tca gga ttt ttc aag       1104
Phe Asn Lys Pro Thr Phe Thr Lys Thr Tyr Leu Ser Gly Phe Phe Lys
        355                 360                 365 aaa aag cgt acc tat acg aat cca gat act aac ctc cac gga gaa act       1152
Lys Lys Arg Thr Tyr Thr Asn Pro Asp Thr Asn Leu His Gly Glu Thr
    370                 375                 380 cgg ccg att att gat act gac atc tat gat aaa gtt atg ccg atg aga       1200
Arg Pro Ile Ile Asp Thr Asp Ile Tyr Asp Lys Val Met Pro Met Arg
385                 390                 395                 400
```

| | | |
|---|---|---|
| att cct gta gtt cct ctg att aaa gct gta att act aaa aat ttt gat<br>Ile Pro Val Val Pro Leu Ile Lys Ala Val Ile Thr Lys Asn Phe Asp<br>405 410 415 | | 1248 |
| tta gct aat gaa cta ggg ttt tta gag gtt tgt ggt gaa gat ttc gcc<br>Leu Ala Asn Glu Leu Gly Phe Leu Glu Val Cys Gly Glu Asp Phe Ala<br>420 425 430 | | 1296 |
| tta ccc act ctt ata gat cca tct aaa aca gaa atg ctt acc ata gtc<br>Leu Pro Thr Leu Ile Asp Pro Ser Lys Thr Glu Met Leu Thr Ile Val<br>435 440 445 | | 1344 |
| aag gaa tcc tta ata gag tac gcc aag gaa tca ggg atc cta act ccc<br>Lys Glu Ser Leu Ile Glu Tyr Ala Lys Glu Ser Gly Ile Leu Thr Pro<br>450 455 460 | | 1392 |
| cat caa gat<br>His Gln Asp<br>465 | | 1401 |

<210> SEQ ID NO 2
<211> LENGTH: 467
<212> TYPE: PRT
<213> ORGANISM: Chlamydia pneumoniae

<400> SEQUENCE: 2

Met Lys Ile Thr Val Asn Arg Gly Leu Asp Leu Ser Leu Gln Gly Ser
 1               5                  10                  15

Pro Lys Glu Ser Gly Phe Tyr Asn Lys Ile Asp Pro Glu Phe Val Ser
             20                  25                  30

Ile Asp Leu Arg Pro Phe Gln Pro Leu Ser Leu Lys Leu Lys Val Glu
         35                  40                  45

Gln Gly Asp Ala Val Cys Ser Gly Ala Pro Ile Ala Glu Tyr Lys His
     50                  55                  60

Phe Pro Asn Thr Tyr Ile Thr Ser His Val Ser Gly Val Val Thr Ala
 65                  70                  75                  80

Ile Arg Arg Gly Asn Lys Arg Ser Leu Leu Asp Val Ile Lys Lys
                 85                  90                  95

Thr Pro Gly Pro Thr Ser Thr Glu Tyr Thr Tyr Asp Leu Gln Thr Leu
                100                 105                 110

Ser Arg Ser Asp Leu Ser Glu Ile Phe Lys Glu Asn Gly Leu Phe Ala
            115                 120                 125

Leu Ile Lys Gln Arg Pro Phe Asp Ile Pro Ala Ile Pro Thr Gln Thr
        130                 135                 140

Pro Arg Asp Val Phe Ile Asn Leu Ala Asp Asn Arg Pro Phe Thr Pro
145                 150                 155                 160

Ser Pro Glu Lys His Leu Ala Leu Phe Ser Arg Glu Glu Gly Phe
                165                 170                 175

Tyr Val Phe Val Val Gly Val Arg Ala Ile Ala Lys Leu Phe Gly Leu
                180                 185                 190

Arg Pro His Ile Val Phe Arg Asp Arg Leu Thr Leu Pro Thr Gln Glu
            195                 200                 205

Leu Lys Thr Ile Ala His Leu His Thr Val Ser Gly Pro Phe Pro Ser
        210                 215                 220

Gly Ser Pro Ser Ile His Ile His Ser Val Ala Pro Ile Thr Asn Glu
225                 240

Lys Glu Val Val Phe Thr Leu Ser Phe Gln Asp Val Leu Thr Ile Gly
                245                 250                 255

His Leu Phe Leu Lys Gly Arg Ile Leu His Glu Gln Val Thr Ala Leu
            260                 265                 270

-continued

```
Ala Gly Thr Ala Leu Lys Ser Ser Leu Arg Arg Tyr Val Ile Thr Thr
            275                 280                 285

Lys Gly Ala Ser Phe Ser Ser Leu Ile Asn Leu Asn Asp Ile Ser Asp
        290                 295                 300

Asn Asp Thr Leu Ile Ser Gly Asp Pro Leu Thr Gly Arg Leu Cys Lys
305                 310                 315                 320

Lys Glu Glu Pro Phe Leu Gly Phe Arg Asp His Ser Ile Ser Val
                325                 330                 335

Leu His Asn Pro Thr Lys Arg Glu Leu Phe Ser Phe Leu Arg Ile Gly
            340                 345                 350

Phe Asn Lys Pro Thr Phe Thr Lys Thr Tyr Leu Ser Gly Phe Phe Lys
            355                 360                 365

Lys Lys Arg Thr Tyr Thr Asn Pro Asp Thr Asn Leu His Gly Glu Thr
        370                 375                 380

Arg Pro Ile Ile Asp Thr Asp Ile Tyr Asp Lys Val Met Pro Met Arg
385                 390                 395                 400

Ile Pro Val Val Pro Leu Ile Lys Ala Val Ile Thr Lys Asn Phe Asp
                405                 410                 415

Leu Ala Asn Glu Leu Gly Phe Leu Glu Val Cys Gly Glu Asp Phe Ala
            420                 425                 430

Leu Pro Thr Leu Ile Asp Pro Ser Lys Thr Glu Met Leu Thr Ile Val
            435                 440                 445

Lys Glu Ser Leu Ile Glu Tyr Ala Lys Glu Ser Gly Ile Leu Thr Pro
        450                 455                 460

His Gln Asp
465
```

<210> SEQ ID NO 3
<211> LENGTH: 1344
<212> TYPE: DNA
<213> ORGANISM: Chlamydia pneumoniae
<220> FEATURE:
<221> NAME/KEY: CDS
<222> LOCATION: (1)..(1344)
<223> OTHER INFORMATION: CPN100605

<400> SEQUENCE: 3

```
att aca gtc aat cgg ggt tta gat tta tcc tta caa ggg tct ccc aaa      48
Ile Thr Val Asn Arg Gly Leu Asp Leu Ser Leu Gln Gly Ser Pro Lys
  1               5                  10                  15 gaa tct ggt ttc tat aac aaa atc gat cca gaa ttc gta tct ata gac      96
Glu Ser Gly Phe Tyr Asn Lys Ile Asp Pro Glu Phe Val Ser Ile Asp
             20                  25                  30 tta agg cca ttc caa cct tta tct ctt aaa ctt aag gta gag caa gga     144
Leu Arg Pro Phe Gln Pro Leu Ser Leu Lys Leu Lys Val Glu Gln Gly
         35                  40                  45 gat gcg gtc tgt tca gga gct cct ata gca gaa tac aag cac ttt cct     192
Asp Ala Val Cys Ser Gly Ala Pro Ile Ala Glu Tyr Lys His Phe Pro
     50                  55                  60 aac acc tac att acc tct cac gtt tca gga gta gtt acc gct ata cga     240
Asn Thr Tyr Ile Thr Ser His Val Ser Gly Val Val Thr Ala Ile Arg
 65                  70                  75                  80 cgt gga aat aaa cgt tct ctt tta gat gtc atc att aag aaa act cct     288
Arg Gly Asn Lys Arg Ser Leu Leu Asp Val Ile Ile Lys Lys Thr Pro
                 85                  90                  95 ggt cct aca tct aca gaa tat acg tat gat ctc caa act ctc tca cgt     336
Gly Pro Thr Ser Thr Glu Tyr Thr Tyr Asp Leu Gln Thr Leu Ser Arg
            100                 105                 110
```

-continued

```
tca gat ctt tcc gaa atc ttt aag gaa aat ggg ctc ttt gca tta atc      384
Ser Asp Leu Ser Glu Ile Phe Lys Glu Asn Gly Leu Phe Ala Leu Ile
        115                 120                 125 aaa caa cgt cct ttt gat att ccc gca att cca aca caa act ccg aga      432
Lys Gln Arg Pro Phe Asp Ile Pro Ala Ile Pro Thr Gln Thr Pro Arg
130                 135                 140 gat gtt ttc atc aat tta gct gac aat cgt cct ttt act cca agc cca      480
Asp Val Phe Ile Asn Leu Ala Asp Asn Arg Pro Phe Thr Pro Ser Pro
145                 150                 155                 160 gaa aaa cat ctg gct ctc ttt tcc tct aga gaa gaa gga ttt tat gta      528
Glu Lys His Leu Ala Leu Phe Ser Ser Arg Glu Glu Gly Phe Tyr Val
        165                 170                 175 ttt gtg gta gga gtt cga gct ata gct aaa ctt ttt gga ctc cgt cct      576
Phe Val Val Gly Val Arg Ala Ile Ala Lys Leu Phe Gly Leu Arg Pro
        180                 185                 190 cat ata gtt ttc aga gat cgt tta act cta cct acg caa gaa cta aag      624
His Ile Val Phe Arg Asp Arg Leu Thr Leu Pro Thr Gln Glu Leu Lys
        195                 200                 205 aca att gct cac ctt cat acc gtt tcg gga cca ttc ccc tct gga tct      672
Thr Ile Ala His Leu His Thr Val Ser Gly Pro Phe Pro Ser Gly Ser
    210                 215                 220 cca tcg ata cat att cac agc gta gcc cct att acc aat gag aaa gaa      720
Pro Ser Ile His Ile His Ser Val Ala Pro Ile Thr Asn Glu Lys Glu
225                 230                 235                 240 gtg gta ttc aca ctg tca ttt caa gat gtc ctt act att ggc cat ctt      768
Val Val Phe Thr Leu Ser Phe Gln Asp Val Leu Thr Ile Gly His Leu
                245                 250                 255 ttc tta aag gga aga att ctg cac gag caa gtc aca gca ctt gct ggt      816
Phe Leu Lys Gly Arg Ile Leu His Glu Gln Val Thr Ala Leu Ala Gly
            260                 265                 270 act gca cta aaa agt tct cta aga cgc tat gtg att act aca aaa gga      864
Thr Ala Leu Lys Ser Ser Leu Arg Arg Tyr Val Ile Thr Thr Lys Gly
        275                 280                 285 gct agc ttc tct agt tta atc aat ctt aat gac atc tcg gat aac gat      912
Ala Ser Phe Ser Ser Leu Ile Asn Leu Asn Asp Ile Ser Asp Asn Asp
290                 295                 300 aca tta att agc gga gat ccc tta aca gga agg cta tgc aaa aag gaa      960
Thr Leu Ile Ser Gly Asp Pro Leu Thr Gly Arg Leu Cys Lys Lys Glu
305                 310                 315                 320 gag gaa ccc ttt tta gga ttt cga gac cat tca att tca gtc tta cac     1008
Glu Glu Pro Phe Leu Gly Phe Arg Asp His Ser Ile Ser Val Leu His
                325                 330                 335 aac cca aca aag cgg gag ttg ttt agc ttt tta aga att ggg ttt aac     1056
Asn Pro Thr Lys Arg Glu Leu Phe Ser Phe Leu Arg Ile Gly Phe Asn
            340                 345                 350 aaa ccg aca ttt aca aaa acc tat ctc tca gga ttt ttc aag aaa aag     1104
Lys Pro Thr Phe Thr Lys Thr Tyr Leu Ser Gly Phe Phe Lys Lys Lys
        355                 360                 365 cgt acc tat acg aat cca gat act aac ctc cac gga gaa act cgg ccg     1152
Arg Thr Tyr Thr Asn Pro Asp Thr Asn Leu His Gly Glu Thr Arg Pro
370                 375                 380 att att gat act gac atc tat gat aaa gtt atg ccg atg aga att cct     1200
Ile Ile Asp Thr Asp Ile Tyr Asp Lys Val Met Pro Met Arg Ile Pro
385                 390                 395                 400 gta gtt cct ctg att aaa gct gta att act aaa aat ttt gat tta gct     1248
Val Val Pro Leu Ile Lys Ala Val Ile Thr Lys Asn Phe Asp Leu Ala
                405                 410                 415 aat gaa cta ggg ttt tta gag gtt tgt ggt gaa gat ttc gcc tta ccc     1296
Asn Glu Leu Gly Phe Leu Glu Val Cys Gly Glu Asp Phe Ala Leu Pro
            420                 425                 430
```

```
act ctt ata gat cca tct aaa aca gaa atg ctt acc ata gtc aag gaa    1344
Thr Leu Ile Asp Pro Ser Lys Thr Glu Met Leu Thr Ile Val Lys Glu
        435                 440                 445
```

<210> SEQ ID NO 4
<211> LENGTH: 448
<212> TYPE: PRT
<213> ORGANISM: Chlamydia pneumoniae

<400> SEQUENCE: 4

```
Ile Thr Val Asn Arg Gly Leu Asp Leu Ser Leu Gln Gly Ser Pro Lys
 1               5                  10                  15

Glu Ser Gly Phe Tyr Asn Lys Ile Asp Pro Glu Phe Val Ser Ile Asp
             20                  25                  30

Leu Arg Pro Phe Gln Pro Leu Ser Leu Lys Leu Lys Val Glu Gln Gly
         35                  40                  45

Asp Ala Val Cys Ser Gly Ala Pro Ile Ala Glu Tyr Lys His Phe Pro
     50                  55                  60

Asn Thr Tyr Ile Thr Ser His Val Ser Gly Val Val Thr Ala Ile Arg
 65                  70                  75                  80

Arg Gly Asn Lys Arg Ser Leu Leu Asp Val Ile Lys Lys Thr Pro
                 85                  90                  95

Gly Pro Thr Ser Thr Glu Tyr Thr Tyr Asp Leu Gln Thr Leu Ser Arg
            100                 105                 110

Ser Asp Leu Ser Glu Ile Phe Lys Glu Asn Gly Leu Phe Ala Leu Ile
        115                 120                 125

Lys Gln Arg Pro Phe Asp Ile Pro Ala Ile Pro Thr Gln Thr Pro Arg
    130                 135                 140

Asp Val Phe Ile Asn Leu Ala Asp Asn Arg Pro Phe Thr Pro Ser Pro
145                 150                 155                 160

Glu Lys His Leu Ala Leu Phe Ser Ser Arg Glu Gly Phe Tyr Val
                165                 170                 175

Phe Val Val Gly Val Arg Ala Ile Ala Lys Leu Phe Gly Leu Arg Pro
            180                 185                 190

His Ile Val Phe Arg Asp Arg Leu Thr Leu Pro Thr Gln Glu Leu Lys
        195                 200                 205

Thr Ile Ala His Leu His Thr Val Ser Gly Pro Phe Pro Ser Gly Ser
    210                 215                 220

Pro Ser Ile His Ile His Ser Val Ala Pro Ile Thr Asn Glu Lys Glu
225                 230                 235                 240

Val Val Phe Thr Leu Ser Phe Gln Asp Val Leu Thr Ile Gly His Leu
                245                 250                 255

Phe Leu Lys Gly Arg Ile Leu His Glu Gln Val Thr Ala Leu Ala Gly
            260                 265                 270

Thr Ala Leu Lys Ser Ser Leu Arg Arg Tyr Val Ile Thr Thr Lys Gly
        275                 280                 285

Ala Ser Phe Ser Ser Leu Ile Asn Leu Asn Asp Ile Ser Asp Asn Asp
    290                 295                 300

Thr Leu Ile Ser Gly Asp Pro Leu Thr Gly Arg Leu Cys Lys Lys Glu
305                 310                 315                 320

Glu Glu Pro Phe Leu Gly Phe Arg Asp His Ser Ile Ser Val Leu His
                325                 330                 335

Asn Pro Thr Lys Arg Glu Leu Phe Ser Phe Leu Arg Ile Gly Phe Asn
            340                 345                 350
```

-continued

```
Lys Pro Thr Phe Thr Lys Thr Tyr Leu Ser Gly Phe Phe Lys Lys Lys
        355                 360                 365

Arg Thr Tyr Thr Asn Pro Asp Thr Asn Leu His Gly Glu Thr Arg Pro
    370                 375                 380

Ile Ile Asp Thr Asp Ile Tyr Asp Lys Val Met Pro Met Arg Ile Pro
385                 390                 395                 400

Val Val Pro Leu Ile Lys Ala Val Ile Thr Lys Asn Phe Asp Leu Ala
                405                 410                 415

Asn Glu Leu Gly Phe Leu Glu Val Cys Gly Glu Asp Phe Ala Leu Pro
            420                 425                 430

Thr Leu Ile Asp Pro Ser Lys Thr Glu Met Leu Thr Ile Val Lys Glu
        435                 440                 445
```